(12) United States Patent
Strong

(10) Patent No.: US 8,490,472 B2
(45) Date of Patent: Jul. 23, 2013

(54) SYSTEM AND METHOD FOR DETECTING MOISTURE

(75) Inventor: Andrew P. Strong, Romsey (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 408 days.

(21) Appl. No.: 12/445,974

(22) PCT Filed: Mar. 15, 2007

(86) PCT No.: PCT/GB2007/000916
§ 371 (c)(1),
(2), (4) Date: Sep. 9, 2010

(87) PCT Pub. No.: WO2008/047068
PCT Pub. Date: Apr. 24, 2008

(65) Prior Publication Data
US 2010/0319435 A1    Dec. 23, 2010

(30) Foreign Application Priority Data

Oct. 19, 2006  (GB) .................................. 0620752.6

(51) Int. Cl.
*G01N 5/02* (2006.01)
*G01N 25/56* (2006.01)

(52) U.S. Cl.
USPC .................................................. 73/75; 73/73

(58) Field of Classification Search
USPC ................. 73/25.04, 73, 75; 374/10, 137
See application file for complete search history.

(56) References Cited

U.S. PATENT DOCUMENTS

| | | | |
|---|---|---|---|
| 3,938,385 A | 2/1976 | Horwath | |
| 4,270,049 A | 5/1981 | Tanaka et al. | |
| 4,490,053 A | 12/1984 | Coston et al. | |
| 4,845,978 A | 7/1989 | Whitford | |
| 4,978,229 A * | 12/1990 | Hughes | 374/30 |
| 5,036,287 A | 7/1991 | Serwatzky | |
| 6,547,435 B1 * | 4/2003 | Grosswig et al. | 374/137 |
| 7,509,008 B2 * | 3/2009 | Perales et al. | 385/100 |
| 2006/0151042 A1 * | 7/2006 | Stringfellow et al. | 138/125 |
| 2008/0296890 A1 * | 12/2008 | Prescott et al. | 285/47 |

FOREIGN PATENT DOCUMENTS

| | | |
|---|---|---|
| CA | 2666770 A1 | 4/2008 |
| DE | 2443828 A1 | 3/1976 |
| DE | 9318404 U1 | 2/1994 |
| DE | 19509129 A1 | 8/1996 |
| EP | 0989396 A2 | 3/2000 |
| EP | 2074414 A1 | 7/2009 |

(Continued)

OTHER PUBLICATIONS

English Language Abstract of JP 59210340 A, Nov. 29, 1984, Publisher: JPO.*
Decision on Grant dated Oct. 31, 2011 for corresponding KZ Application No. 2009/1575.1 filed Mar. 15, 2007.
European Search Report for European Application No. EP0989396 dated on Mar. 27, 2000, 3 pages.

(Continued)

*Primary Examiner* — Lisa Caputo
*Assistant Examiner* — Roger Hernandez-Prewitt
(74) *Attorney, Agent, or Firm* — Brandon Clark

(57) ABSTRACT

A technique facilitates the detection of moisture. The technique utilizes distributed sensor lines deployed along an insulated vessel, such as an insulated pipe. The sensor lines are used to measure temperature and to determine a differential temperature across the insulation between the sensor lines. Changes in the differential temperature can be detected, and those changes are used to determine whether moisture has intruded into a specific region of the insulation.

19 Claims, 4 Drawing Sheets

FOREIGN PATENT DOCUMENTS

| | | | |
|---|---|---|---|
| GB | 2393791 | A | 4/2004 |
| GB | 2393781 | | 7/2004 |
| GB | 2442981 | A | 4/2008 |
| JP | 59210340 | A * | 11/1984 |
| SU | 1781504 | A1 | 12/1992 |
| WO | 9626425 | A1 | 8/1996 |
| WO | 2008047068 | A1 | 4/2008 |

OTHER PUBLICATIONS

International Search Report for PCT Application No. PCT/GB2007/000916 mailed on May 23, 2007, 4 pages.

Written Opinion for PCT Application No. PCT/GB2007/000916 mailed on Apr. 19, 2009, 6 pages.

* cited by examiner

SYSTEM AND METHOD FOR DETECTING MOISTURE

BACKGROUND OF THE INVENTION

1. Field of the Invention

Corrosion under insulation is problematic in many environments. In oil and gas production plants, process plants, refineries, and chemical plants, for example, corrosion under insulation can be a serious threat to plant integrity. Management of the corrosion under insulation problem can be extremely challenging, because water ingress is difficult to reliably predict and many types of insulation systems can be affected. Additionally, regular inspection and maintenance is difficult and costly, typically involving removal of insulation from process piping. Sometimes, the inspection and maintenance techniques can require shutdown of the plant process.

2. Description of Related Art

Moisture sensors exist but have drawbacks that limit their usefulness in many environments susceptible to corrosion under insulation. Conventional moisture sensors, constructed as point devices using coated, metalized surfaces that undergo a change in electrical impedance when exposed to moisture, are not practical for use in a process environment. Some sensors measure rate of heat dissipation to determine moisture content in a medium, while other sensors measure changes in electrical resistance of an element exposed to moisture, but none of these sensors is practical for use in many process and plant environments. For example, some of these sensors are not particularly helpful in providing guidance as to specific areas of concern along, for example, sections of insulated pipe. Another moisture sensing technique detects hydrogel-induced micro bending in fibers, but such techniques also have limited applicability in process and plant environments. For example, such techniques can be limited to environments in which temperatures only rise to approximately 50° C.

BRIEF SUMMARY OF THE INVENTION

In general, the present invention provides a system and method for detecting the intrusion of moisture into insulation, such as the intrusion of water into insulation used in a plant environment. For example, the technique can be used to enable detection of moisture within process piping insulation and for monitoring conditions, e.g. moisture and temperature, which can lead to corrosion under the insulation. A first distributed sensor line and a second distributed sensor line are positioned along a desired section of insulation, and the differential temperatures are measured across the insulation between the lines. The determination of regional changes in the differential temperatures provides an indication of a potential moisture problem in a specific region or regions of the insulation.

BRIEF DESCRIPTION OF THE DRAWINGS

Certain embodiments of the invention will hereafter be described with reference to the accompanying drawings, wherein like reference numerals denote like elements, and.

DETAILED DESCRIPTION OF THE INVENTION

In the following description, numerous details are set forth to provide an understanding of the present invention. However, it will be understood by those of ordinary skill in the art that the present invention may be practiced without these details and that numerous variations or modifications from the described embodiments may be possible.

The present invention relates to a system and method for detecting and managing corrosion under insulation in insulated equipment, such as vessels for holding and/or carrying fluids. For example, the system can be used along the length of insulated piping or other insulated equipment. The system operates through detection of moisture in the insulation via ongoing evaluation of differential temperatures across the insulation or partial sections of insulation surrounding the piping or other equipment. This automatic, ongoing insulation evaluation affords improved risk assessments for corrosion under insulation. The ongoing evaluation also reduces the requirements for regular inspection and maintenance in, for example, a variety of plants, including oil and gas production/processing plants, refineries, chemical plants and other plants that use insulated vessels in plant operations.

Generally, distributed sensor lines, such as distributed temperature sensing system compatible sensor fibers or sensor cables are deployed through or along the insulation surrounding piping or other equipment such that the sensor lines are separated by at least a portion of the insulation layer. The distributed sensor lines enable a distributed and continuous determination of the differential temperature across the insulation between the sensor lines via, for example, distributed temperature sensing technology. An initial temperature differential is established between the sensor lines as a reference temperature differential. This enables ongoing detection of any changes in the temperature differential, which can be indicative of moisture intruding on that particular region of insulation. If, for example, a region of the insulation is wetted via intrusion of water or other wetting agent, the sensor lines detect a reduction in temperature differential for that region due to impairment of the insulating properties of the insulation resulting from the moisture.

Figure 1:
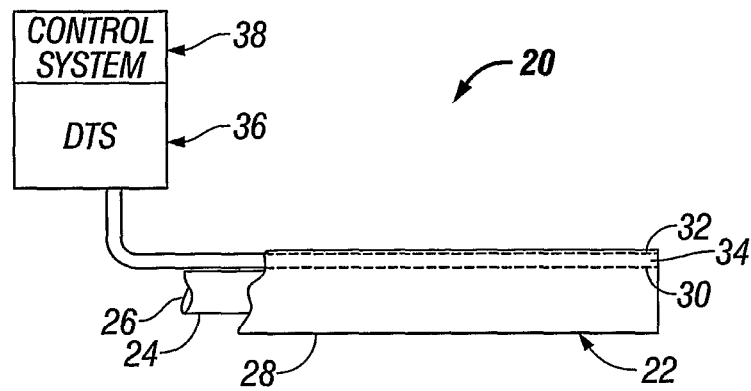
FIG. 1 is a schematic view of an insulated apparatus combined with a moisture detection system, according to an embodiment of the present invention.

Referring generally to FIG. 1, a system 20 is illustrated as an example of a variety of systems that can be found in plant environments or other environments that use insulated equipment. In this embodiment, system 20 comprises an insulated equipment component in the form of an insulated vessel 22 having a vessel 24 with a vessel wall 26 covered by insulation 28. By way of specific example, vessel 24 may comprise a pipe, and insulation 28 may be formed as a layer of insulation around the piping 24. At least two distributed sensor lines 30 and 32 are deployed along the insulated vessel 22 and separated by a section 34 of insulation 28. Additional distributed sensor lines can be deployed through insulation 28 if differential temperatures and moisture detection are sought along other areas of the insulated vessel or if a backup sensor system is desired for a specific application.

In many applications, the distributed sensor lines 30, 32 are deployed with fairly uniform spacing therebetween to establish a uniform reference differential temperature. The routing of the sensor lines along or through the insulation can vary from one application to another. In the embodiment illustrated, the sensor lines 30 and 32 are spaced generally uniformly and routed in a longitudinal direction along piping 24.

The distributed sensor lines 30 and 32 may comprise distributed temperature sensing compatible sensor lines coupled into a distributed temperature sensing system 36. By way of example, distributed sensor lines 30 and 32 may comprise distributed temperature sensing system compatible sensor fibers or distributed temperature sensing system compatible cables deployed along insulated vessel 22. The distributed temperature sensing system 36 and the ongoing measurement of differential temperatures along insulated vessel 22 may be automatically controlled via a control system 38. Control system 38 enables continuous measurement of temperature along each distributed sensor line 30 and 32, establishment of differential temperatures between the sensor lines, and determination of any changes in the differential temperature at any region along insulated vessel 22. Additionally, control system 38 enables the measurement of temperature and the determination of differential temperatures continuously and in real time if desired for a specific application.

Figure 2:
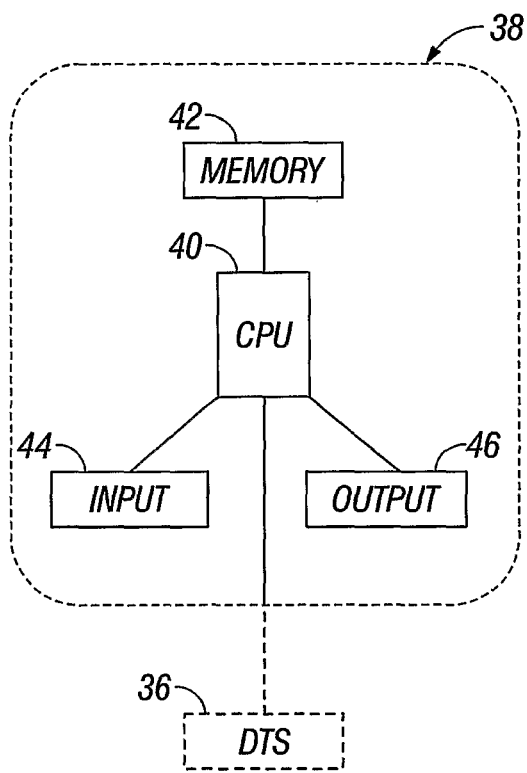
FIG. 2 is a diagrammatic representation of a processor based control system that can be used to carry out all or part of the methodology for determining the intrusion of moisture, according to an embodiment of the present invention.

An example of an automated control system 38 is illustrated diagrammatically in FIG. 2. In this embodiment, automated control system 38 may be a computer-based system having a central processing unit (CPU) 40. CPU 40 may be operatively coupled to distributed temperature sensing system 36, and may comprise a memory 42, an input device 44, and an output device 46. Input device 44 may comprise a variety of devices, such as a keyboard, mouse, voice-recognition unit, touchscreen, other input devices, or combinations of such devices. Output device 46 may comprise a visual and/or audio output device, such as a monitor having a graphical user interface. Additionally, the processing of the information from distributed sensor lines 30 and 32 may be done on a single device or multiple devices at the system location, at a centralized plant location, at locations remote from the plant, or at multiple locations.

Figure 3:
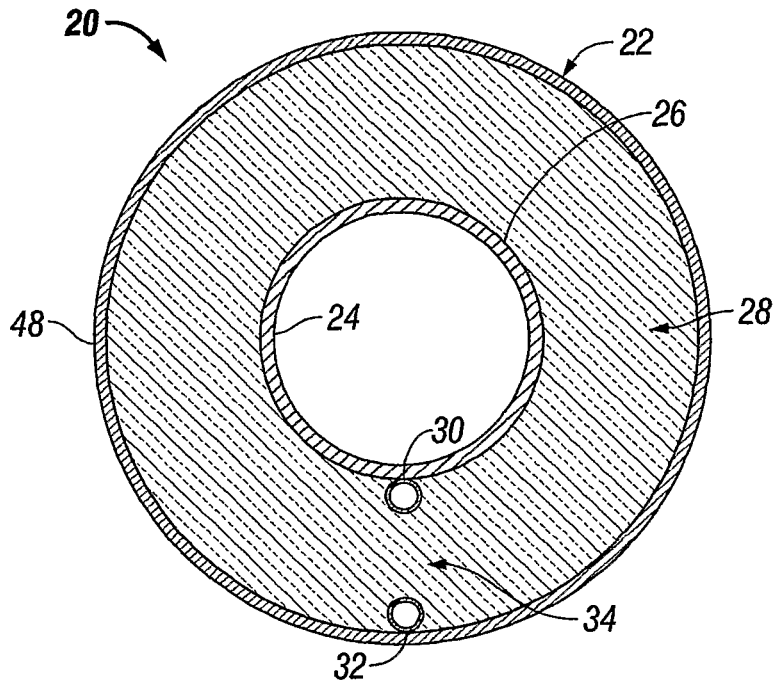
FIG. 3 is a cross-sectional view of an insulated vessel having spaced sensor lines, routed along a layer of insulation, for determining differential temperatures along the layer, according to an embodiment of the present invention.
Figure 4:
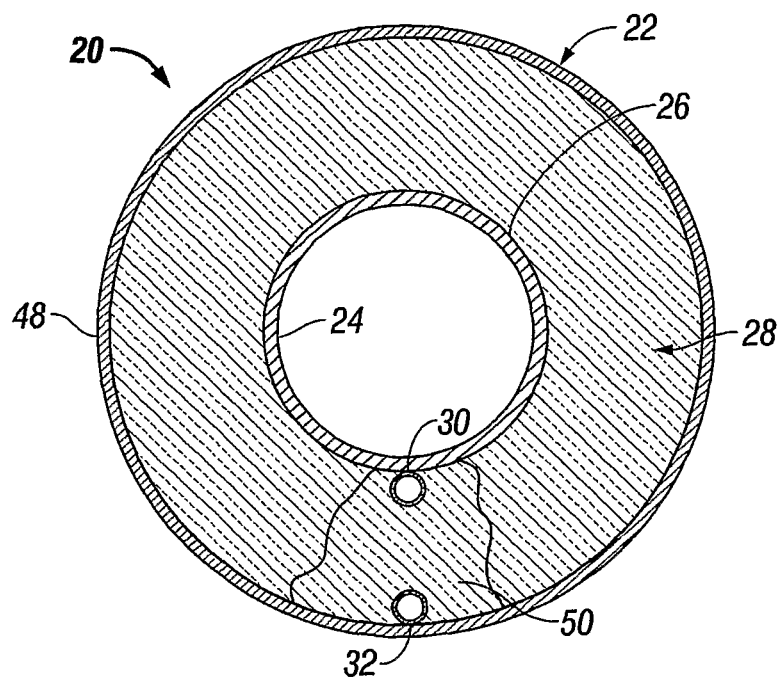
FIG. 4 is a view similar to that of FIG. 3, but showing the formation of moisture in a specific region.

Referring generally to FIGS. 3 and 4, a specific example of system 20 is illustrated. In this example, insulation 28 is arranged in a layer around pipe 24 defined by the vessel or pipe wall 26. In this example, both distributed sensor lines 30 and 32 are routed generally longitudinally through insulation layer 28 with a portion of the insulation layer, i.e. insulation section 34, disposed between the sensor lines. Distributed sensor line 30 is deployed radially inward of distributed sensor line 32 generally adjacent an exterior of the wall 26 defining pipe 24. Distributed sensor line 32 is deployed proximate a radially exterior surface of insulation layer 28. However, the distributed sensor lines 30 and 32 can be deployed at different locations on or through the insulation layer 28. In this embodiment, insulation layer 28 also comprises an outer protective sheath 48, and both distributed sensor lines 30 and 32 are located radially inward of outer protective sheath 48.

The distributed sensor lines 30 and 32 can measure temperatures along their length through insulation layer 28 over, for example, the distance spanned by pipe 24. By using distributed temperature sensing system compatible fibers or cables, the system can be designed to measure temperatures up to and even higher than 200° C. Distributed temperature sensing system 36 and control system 38 are used in determining the differential temperatures between sensor lines 30 and 32 along the length of the sensor lines, e.g. along the entire length of pipe 24. If moisture intrudes into insulation 28 to form a wetted region 50, as illustrated in FIG. 4, the insulating properties of the insulation layer become impaired. The impaired insulating properties reduce the differential temperature in wetted region 50, and the reduced differential temperature is detected and processed by distributed temperature sensing system 36 and control system 38. Once the change in differential temperature is detected by the system, the system can provide an audible and/or visual output via, for example, output 46 for review by an operator. The pinpointed location of a change in the differential temperature enables the operator to examine and attend to the specific region of the insulated vessel potentially experiencing the problem.

Figure 5:
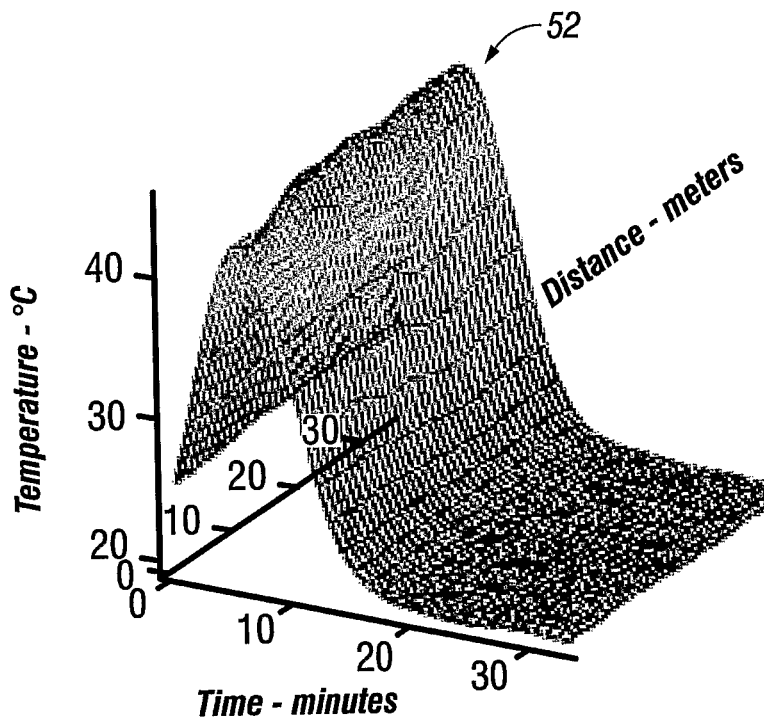
FIG. 5 is a graphical representation of temperatures measured along one of the sensor lines, according to an embodiment of the present invention.
Figure 6:
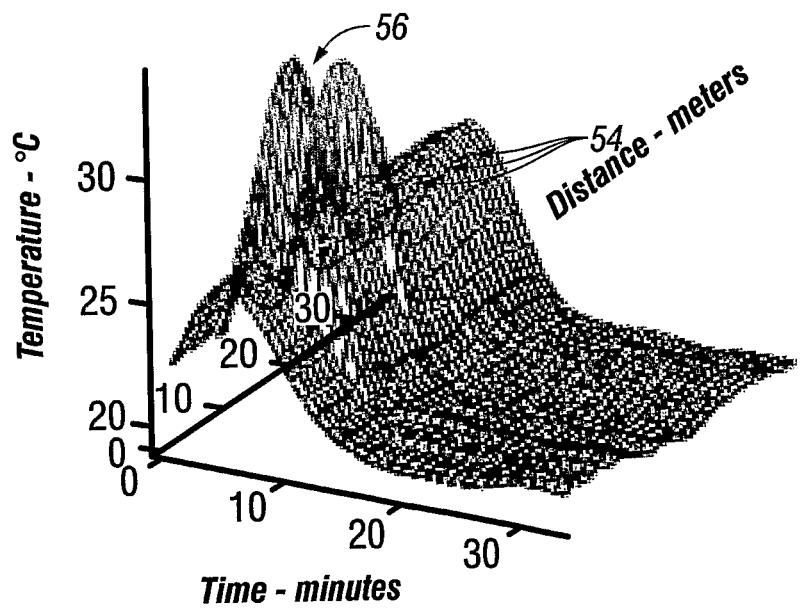
FIG. 6 is a graphical representation of temperatures measured along a second sensor line, the graph illustrating temperature peaks indicative of reduced differential temperature and the potential intrusion of moisture, according to an embodiment of the present invention.

By way of example, the distributed temperature sensing system 36 and control system 38 can be used to provide continuous, real-time detection of temperatures and a determination of differential temperatures along each of the distributed sensor lines 30 and 32, as illustrated graphically in FIGS. 5 and 6. The shape of the graphs, of course, varies according to the positioning of sensor lines 30 and 32, the type of vessel 24, the type and temperature of fluid contained in or passing through the vessel, the constant or intermittent nature of fluid passing through the vessel, e.g. piping, 24, the type of insulation used in insulation layer 28, and other factors affecting the ultimate shape of the graphs. Accordingly, the graphical representations in FIGS. 5 and 6 are simply one example of temperatures, temperature differentials, and changes in temperature differentials for a heated fluid that is passed through an insulated pipe. However, the graphical representations are illustrative of the type of information provided to distributed temperature sensing system 36 and control system 38 via distributed sensor lines 30 and 32.

In this particular example, distributed sensor line 30 is deployed adjacent pipe 24, as described with respect to FIGS. 3 and 4. Upon passage of a heated fluid through pipe 24, distributed sensor line 30 detects and measures temperatures along the length of the insulated pipe as represented by graph peaks 52 of FIG. 5. Similarly, distributed sensor line 32 detects and measures temperatures along the radially outlying region of insulation layer 28, as represented by graph peaks 54 of FIG. 6. However, in wetted regions, such as wetted region 50 illustrated in FIG. 4, the efficiency of the insulation layer is reduced. The reduced efficiency causes temperature increases that are detected and measured by distributed sensor line 32 in the wetted region(s) along the insulated piping. The increased temperatures, as represented by graph peaks 56, result in a reduced differential temperature between distributed sensor lines 30 and 32 for those specific regions. Accordingly, by measuring the temperatures along each distributed sensor line 30 and 32 and determining changes, e.g. reductions, in differential temperatures at specific regions, the system 20 can be used to provide an operator with indicated regions where moisture has potentially intruded into insulation 28.

Figure 7:
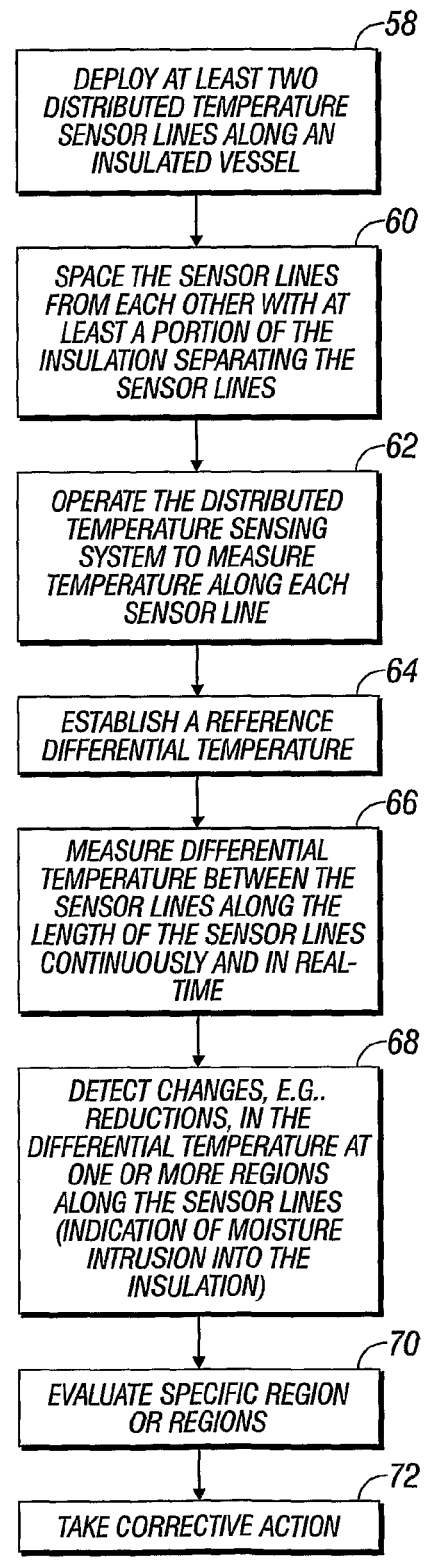
FIG. 7 is a flowchart illustrating an embodiment of the methodology that can be used to determine the wetting of a region of insulation, according to an embodiment of the present invention.

An example of an implementation of system 20 and the methodology used in operating system 20 is illustrated by the flowchart of FIG. 7. It should be noted, however, that this is one example of the methodology, and changes and/or additions can be made to accommodate different environments, components and application parameters. In this example, at least two distributed temperature sensor lines are initially deployed along an insulated vessel, as illustrated by block 58. The distributed sensor lines are spaced from each other such that at least a portion of the insulation surrounding the vessel separates the distributed sensor lines, as illustrated by block 60. The distributed sensor lines can be routed along the outer extents of the insulation or through interior regions of the insulation. Additionally, the distributed sensor lines can be routed along generally straight or circuitous paths along an exterior or an interior of the vessel, depending on the specific application in which the insulated vessel is used. The spacing between the sensor lines also can be constant or can undergo changes to, for example, accommodate unique shapes of the insulated vessel.

Upon constructing the insulated vessel with the appropriate distributed sensor lines, the system is operated to enable the distributed temperature sensing system 36 to measure temperatures along each distributed sensor line 30 and 32, as illustrated by block 62. During this initial run, the temperatures gathered can be used to establish reference differential temperatures along the distributed sensor lines, as illustrated by block 64. In this particular example, the process is ongoing, e.g. heated fluid is continually run through pipe 24, and differential temperatures between the sensor lines are determined continuously and on a real-time basis, as illustrated by block 66. The temperature measurement and the determination of differential temperatures can be done along the entire length of the insulated pipe.

As the process/application continues, temperatures are continuously measured and compared to determine any changes in temperature differentials. If moisture intrudes on an area of insulation, the differential temperature changes and those changes, e.g. reductions, in differential temperature are detected by distributed temperature sensing system 36. The detected changes can be for one or more specific regions along the distributed sensor lines, as illustrated by block 68. An operator, such as a plant operator, is then able to evaluate the specific region or regions to determine whether any areas of insulation have actually become wetted, as illustrated by block 70. Depending on the extent and location of the intruding moisture, appropriate corrective action can be taken to reduce or eliminate potential corrosion under insulation, as illustrated by block 72.

The specific plant processes in which the moisture detection system is implemented can vary widely. Additionally, the shape, size and function of the insulated vessels may vary from one plant to another or from one plant section to another. The type of distributed sensor lines, e.g. fibers or cables, can vary and the specific type of insulation used for a given application can vary depending on the environment in which a process is carried out as well as the specific parameters of that process. Additionally, the specific type of distributed temperature sensor system and control system used can vary according to application requirements, available technology, and changes in technology.

Accordingly, although only a few embodiments of the present invention have been described in detail above, those of ordinary skill in the art will readily appreciate that many modifications are possible without materially departing from the teachings of this invention.

What is claimed is:

1. A system, comprising:
   a component having a longitudinally extending component wall and an insulating layer along the length of the component wall; and
   a distributed temperature sensing system comprising a first sensor line and a second sensor line radially separated by insulation of the insulation layer and extending longitudinally along length of the component wall, wherein the distributed temperature sensing system determines changes in the differential temperature between the first and second sensor lines to detect moisture in a portion of the insulation layer, and wherein the first sensor line and the second sensor line are configured to respond continuously along their respective lengths to temperature to detect moisture in any portion of the insulation layer between the first and second sensor lines.

2. The system of claim 1, wherein the component comprises a pipe.

3. The system of claim 2, wherein the first sensor line is positioned adjacent the pipe and the second sensor line is positioned along a radially external portion of the insulation layer.

4. The system of claim 1, wherein the insulation layer comprises an outer protective sheath, and the first and the second sensor lines are located radially inward of the outer protective sheath.

5. The system of claim 2, wherein the distributed temperature sensing system continuously determines the differential temperature to detect moisture in a specific region of the insulation layer.

6. The system of claim 1, wherein the first sensor line and the second sensor line comprise sensor fibers configured to respond continuously along their respective lengths to temperature.

7. The system of claim 1, wherein the first sensor line and the second sensor line comprise sensor cables configured to respond continuously or their respective lengths to temperature.

8. The system of claim 1, wherein the distributed temperature sensing system determines changes in the differential temperature between the first and second sensor lines continuously in real time.

9. A method of reducing corrosion under insulation comprising:
   deploying individual distributed temperature sensor lines along the length of a structure with insulation disposed between the individual distributed temperature sensor lines, the individual distributed temperature sensor lines configured to respond continuously along their respective lengths to temperature, the individual distributed temperature sensor lines spaced radially apart from each other; and
   measuring differential temperatures at continuous locations between the individual distributed temperature sensor lines to determine any region of the insulation exposed to a wetting agent.

10. The method of claim 9, wherein deploying comprises deploying the individual distributed temperature sensor lines through the insulation.

11. The method of claim 10, wherein the structure is a pipe, and the method further comprising locating the insulation around the pipe.

12. The method of claim 11, further comprising forming the insulation as a layer having an outer protective sheath.

13. The method of claim 11, wherein the deploying comprises deploying a pair of individual distributed temperature sensor lines along the insulation with a portion of the insulation separating the distributed temperature sensor lines in a radial direction.

14. The method of claim 13, wherein deploying comprises deploying the pair of individual distributed temperature sensor lines such that a first distributed temperature sensor line lies proximate the pipe and a second distributed temperature sensor line is radially spaced from the first distributed sensor line and lies proximate an exterior of the insulation layer.

15. The method of claim 9, wherein measuring differential temperatures comprises:
- establishing an initial temperature differential; and
- using the initial temperature differential as a reference temperature differential.

16. The method of claim 9, wherein measuring differential temperatures comprises determining regions in which the differential temperature is reduced as a result of exposure to the wetting agent.

17. The method of claim 9, wherein measuring differential temperatures comprises measuring continuously.

18. The method of claim 17, wherein measuring differential temperatures comprises measuring in real time.

19. The method of claim 9, further comprising determining changes in the differential temperatures by:
- determining a reduction in differential temperature along a pair of the individual distributed temperature sensor lines; and
- using the reduction in differential temperature to indicate the region experiencing wetting.

* * * * *